(12) United States Patent
Baumgartner

(10) Patent No.: US 6,949,344 B1
(45) Date of Patent: Sep. 27, 2005

(54) HAIR ANALYSIS METHOD

(75) Inventor: Werner Andreas Baumgartner, Malibu, CA (US)

(73) Assignee: Psychemical Corporation, Action, MA (US)

( * ) Notice: Subject to any disclaimer, the term of this patent is extended or adjusted under 35 U.S.C. 154(b) by 0 days.

(21) Appl. No.: 07/737,703

(22) Filed: Jul. 30, 1991

Related U.S. Application Data

(63) Continuation-in-part of application No. 07/285,123, filed on Dec. 16, 1988, now Pat. No. 5,324,642, which is a continuation-in-part of application No. 07/215,591, filed on Jul. 6, 1988, now abandoned, which is a continuation-in-part of application No. 07/138,515, filed on Dec. 28, 1987, now abandoned.

(51) Int. Cl.$^7$ .............................................. G01N 33/53
(52) U.S. Cl. ............................ 435/7.1; 435/23; 435/24; 435/265; 435/267; 436/175; 436/177; 436/518; 436/816; 436/825; 436/901
(58) Field of Search .............................. 435/7.1, 23, 24, 435/265, 267, 961, 962; 436/175, 177, 816, 518, 825, 901

(56) References Cited

U.S. PATENT DOCUMENTS

| | | | | |
|---|---|---|---|---|
| 4,762,706 A | * | 8/1988 | McCormick et al. | .......... 424/85 |
| 4,853,335 A | * | 8/1989 | Olsen | .......... 436/527 |
| 4,939,240 A | * | 7/1990 | Chu et al. | .......... 530/387 |
| 5,288,611 A | * | 2/1994 | Kohne | .......... 435/6 |

FOREIGN PATENT DOCUMENTS

| | | | |
|---|---|---|---|
| CA | 2004068 | * | 6/1990 |
| ES | 0187862 | * | 11/1983 |

OTHER PUBLICATIONS

Saito et al., "Characteristics of n–octyl β–D–thioglucopyranoside, a new non–ionic detergent useful for membrane biochemistry," *Biochem. J.*, vol. 222, pp. 829–832 (1984).*
Holmes, A.N., "Degradation of Human Hair by Papain", *Textile Research Journal*, (Aug. 1964), pp. 706–712.*
Warner, Ann, "Interference of Common Household Chemicals in Immunoassay Methods for Drugs of Abuse", *Clin Chem*, vol. 35, No. 4, (1989), pp. 648–651.*
Ahmed et al., "Characterization of Cocaine Binding Protein in Human Placenta", *Life Sciences*, vol. 46, pp. 553–561, (1990).*
Zahler et al., *J. Biol. Chem.*, vol. 243, No. 4, (1968), pp. 716–719.*
"Cleland's Reagent", Calbiochem Doc. No. 4926–285, pp. 11, 22, and 24–25.*
Helenius, et al. "Properties of Detergents", in *Methods in Enzymology*, vol. 56, Colowick et al., EDS, Academic Press, New York, (1979), pp. 734–749.*
Kimmel et al., *Advances in Enzymology*, vol. 19, F.F. Nord, Ed., (1957), pp. 267–334.*
Offidani et al., *Forensic Science International*, vol. 41, No. 1/2, pp. 35–39, (1989).*
Geisen et al., *Hair Research*, [Proc. Int. Congr.], 1$^{st}$, Meeting Date 1979, pp. 138–139, (1981).*
Valente et al., *Clin. Chem*, vol. 27, No. 11, pp. 1952–1953, (1981).*
Gainer et al., Virology, vol. 45, pp. 91–100, (1971).*
Neugebauer, "A Guide to the Properties and Uses of Detergents in Biology and Biochemistry," Calbiochem Biochemicals, pp. 13 and 30, (1988).*

* cited by examiner

*Primary Examiner*—Long V. Le
*Assistant Examiner*—Nelson Yang
(74) *Attorney, Agent, or Firm*—Ropes & Gray LLP

(57) ABSTRACT

A method the direct analysis of an analyte in keratinized structures, e.g., hair and fingernails, which comprises preparing a mixture containing a low redox potential activator compound such as dithiothreitol or dithioerythritol, an enzyme suitable for the digestion of the keratin structure, a sample of the keratin structure and a biological detergent that aids the digestion of the keratinized structure at a relatively low pH, e.g., between about 6.2 and 8; permitting the enzyme to at least substantially digest the sample of keratin structure, and subjecting the digest solution to analysis, preferably by radioimmunoassay, to determine the identity and amount of analyte in the keratin structure sample. To accelerate the method, cupric sulfate may be added to the mixture after degradation of the keratin sample. The enzyme may be a peptidase, endopeptidase or proteinase, with papain, chymopapain, and proteinase K being preferred for use in the invention. The preferred biological detergents include betaine, sulfo-betaine, alkyl-glucosides and bile acids.

12 Claims, No Drawings

HAIR ANALYSIS METHOD

CROSS REFERENCE TO RELATED APPLICATIONS

This application is a continuation-in-part of U.S. application Ser. No. 07/285,123 filed Dec. 16, 1988, now U.S. Pat. No. 5,324,642 which in turn is a continuation-in-part of U.S. application Ser. No. 07/215,591 filed Jul. 6, 1988, now abandoned, which in turn is a continuation-in-part of U.S. application Ser. No. 07/138,515, filed Dec. 28, 1987, now abandoned.

FIELD OF THE INVENTION

This invention relates to an improved analytical method which effectuates the relatively rapid solubilization of hair and direct analysis of organic analytes, e.g., drugs of abuse, present in hair and other keratinized structures, e.g., fingernails and toenails, without effecting the structure of the analyte or being detrimental to biological analyte probes, e.g., antibody, RNA/DNA and bio-receptor probes. The analyte can be analyzed by adding the analyte probe directly to the solubilized keratin structure containing the analyte to determine the identity of the analyte as well as the extent and duration of its consumption by a subject.

BACKGROUND OF THE INVENTION

In the past, hair analysis techniques for the detection of trace metals were developed that purported to provide information on an individual's nutritional status. One objection to the use of these techniques is the difficulty of distinguishing between trace metals deposited in hair from the bloodstream and metals which have become embedded in hair through external contact with, for example, water and cosmetic agents. Consequently, these techniques are not considered useful by the medical community for diagnosing nutritional problems, and therefore have not been considered sufficiently accurate to determine the level of a particular trace metal consumed by a subject.

The problems with previous hair analysis techniques have caused reliance on urine and blood analysis techniques for the detection of ingested chemicals, e.g., drugs-of-abuse, medications and toxic chemicals, in a subject. However, these techniques also are known to be disadvantageous in that the duration and intensity of use or exposure cannot be ascertained. Urine and blood analysis, at best, can provide short term information concerning ingested drugs or chemicals such as drugs-of-abuse. In addition, there are also problems with the interpretation of such results. For example, the detection of a low level of ingested chemical in the urine could mean that a subject ingested a small amount of the drug or chemical very recently or a larger amount several days earlier. Thus, chronic drug use cannot be determined with these methods without repeated testing.

In response to the problems of establishing a reliable and accurate method that would measure both the duration and intensity of use of drugs-of-abuse, medications, toxic chemicals, etc., work performed by Dr. Werner A. Baumgartner, as reported in "Radioimmunoassay of Hair for Determining Opiate Abuse Histories", J. Nucl Med 20:749–752 (1979), determined that long-term histories of exposure to drugs-of-abuse can be obtained through the analysis of mammalian body hair, since these substances are "trapped" within individual hair fibers during their synthesis. In this respect, hair was shown to act like a tape recorder, i.e., past exposure histories can be evaluated through sectional analysis of hair samples. It was found that heroin, once in the bloodstream, will find its way into hair as it is synthesized.

Thus, it was discovered in this study and confirmed by subsequent studies that a variety of chemicals, such as drugs-of-abuse, medications, toxic chemicals, etc., hereinafter collectively referred to as "analyte", are trapped by hair during its synthesis and that these substances are "locked up" in hair for essentially the duration of the hair. This was found to be true for head and body hair as well as for other keratinized structures such as fingernails. Suzuki et al., Forensic Sci. International, 24:9–16, 1984. These entrapped substances cannot be washed out of hair, and are completely released only upon the complete, or nearly complete, destruction of the hair fiber.

Prior art methods of extracting an analyte from hair included subjecting the hair to hot methanol solutions (Baumgartner et al., J. Nucl Med 20, 748, 1979) and by overnight incubation of hair in an alkaline or acid medium. D. Valente, et al., Clinical Chemistry, 1952, Vol. 27, No. 11, 1981. Prior methods also include the use of a mortar and pestle to release the entrapped analyte in conjunction with a solvent.

However, solvent extraction procedures suffer from several problems in accurately determining the presence and amount of an ingested analyte. One of these problems is that the solvent extraction methods frequently remove only a small unknown and variable fraction of the total analyte present in the hair sample. Such methods also tend to be time consuming, and generally involve elevated temperatures which may damage the analyte. Another disadvantage is that different analytes require different solvents for extraction. For example, a hair sample containing morphine, phencyclidine ("PCP"), cocaine and marijuana has to be extracted sequentially with several different solvents, which is a very time consuming procedure, particularly since the solvents have to be evaporated before analysis can proceed.

Other methods and studies pertaining to the degradation of hair and hair analysis include: O. Suzuki. et, al., in a publication by Elsevier Scientific Publishers Ireland Ltd., discloses a method for detecting methamphetamine and amphetamine in nail clippings or hair in which the substance was first washed in a mixture of methanol and water and dissolved in sodium hydroxide, followed by analysis of the extracted drug.

A.W. Holmes, in Textile Research Journal, 706–712, August 1964, discloses the degradation of human hair by papain using sodium sulfite as enzyme activator.

Annette M. Baumgartner, et al., in the Journal of Nuclear Medicine, 20:748–752, 1979, discloses the extraction of morphine and heroin from hair by pulverizing hair with a mortar and pestle followed by treatment with methanol.

D. Valente, et al., in Clinical Chemistry, Vol. 27, No. 11, 1981, discloses Dr. Baumgartner's technique of subjecting hair to a treatment of hot methanol to effectuate extraction of drugs of abuse as well as the author's technique of extracting morphine in an acid or alkaline medium.

A.M. Baumgartner, et al., in Journal of Forensic Sciences, p. 576–81, July 1981, discloses the extraction of PCP with mortar and pestle followed by treatment with methanol. The extracted PCP was then analyzed with RIA.

Smith et al., in Journal of Forensic Sciences, Vol. 26, No. 3, July 1981, pp. 582–586, disclose the testing of hair for the presence of phenobarbital, in which a single head hair was washed, dried, cut in 2 mm lengths and added to 0.2 ml 0.1% SDS/saline solution, and a sample assayed by radioimmunoassay.

W.A. Baumgartner. Black, et al., in J. Nucl Med 23: 790–892, 1982, discloses the extraction of cocaine from hair samples by refluxing the hair samples in ethanol followed by RIA analysis.

Ishiyama, et al., in Journal of Forensic Sciences, Vol. 28, No. 2, April 1983, pp. 380–385, disclose a method whereby hair from methamphetamine addicts was dissolved using 1.5 N hydrochloric acid at a pH between 1 and 2, followed by analysis using a gas chromatograph and mass spectrometry.

K. Puschel, et al., in Forensic Science International, 21 (1983) 181–186, discloses the dissolving of hair samples by exposure to sodium hydroxide and heat followed by analysis for the presence of morphine by RIA.

O. Suzuki, et al., in Journal of Forensic Sciences, Vol. 29, No. 2, April 1984, pp. 611–617, discloses the detection of methamphetamine and amphetamine in a single human hair by gas chromatography and chemical ionization mass spectrometry. The hair sample was first dissolved in a sodium hydroxide solution to which was added N-methylbenzylamine.

N.J. Haley et al., in Clin. Chem. 31/10, 1598–1600 (1985), discloses the analysis of hair for nicotine and cotinine, in which washed hair samples were dissolved in a buffer solution containing gelatin, sodium chloride, Tris and EDTA, and adjusted to pH 7.4. Samples were then analyzed by radioimmunoassay.

Sramek, Baumgartner, et al., in A. M. J. Psychiatry 142:8, August 1985, discloses the analysis of hair samples of psychiatric patients with methanol extraction and radioimmunoassay.

Baumgartner, et al., in Clinical Nuclear Medicine, vol. 10, September 1985, discloses the benefits of extracting entrapped drugs of abuse from hair followed by RIA analysis.

Gill, et al., in Nature, Vol. 318, p. 577 (1985) discloses the use of an SDS/proteinase k/dithiothreital mixture to extract DNA from whole blood, whole semen, vaginal fluid, hair roots, bloodstains and semen stains. The article states that "no DNA could be isolated from hair shafts".

Smith et al., in J. Forensic Sci. 1986, 31(4), 1269–73, discloses the detection of cocaine in perspiration, menstrual blood stains and hair using RIA.

M. Margio, et al., in "Determination of Morphine and Other Opioids in the Hair of Heroin Addicts by HPLC and MS/MS" at the International Conference, University of Verona, Jun. 25–26, 1986, discloses various methods to assay morphine from hair samples.

M. Marigo, et al., in the Journal of Analytical Toxicology, Vol. 10, July/August 1986, discloses a method for the quantitative determination of morphine contained in the hair of heroin addicts, by means of heat-acid hydrolysis, pre-column dansyl derivatization, straight phase liquid chromatography and fluorescence detection.

Smith, et al., in Journal of Forensic Sciences, Vol. 31, No. 4, October 1986, pp. 1269–1273, disclose a method for the analysis of hair for the presence of drugs whereby hair samples were first washed, cut into small segments, mechanically pulverized for six minutes, refluxed in ethanol and the samples analyzed using radioimmunoassay.

M. Michalodinitrakis, Med. Sci. Law (1987), Vol. 27, No. 1, discloses the detection of cocaine in rats from the analysis of hair samples, which were dissolved upon exposure to 1.5 N HCL, which brought the pH value to 1–2, following incubation with 0.01 N HCl at 37° C. for one hour.

Pelli, et al., in Biomedical and Environmental Mass Spectrometry, Vol. 14, 63–68 (1987) discloses a procedure for the identification of morphine in the hair of heroin addicts in which hair is treated with diethylether and hydrochloric acid followed by dissolution of the dried extract in methanol.

Higuchi et al., in Nature, Vol. 332, p. 543 (1988) disclose a method for dissolving hair at pH 8 by the action of dithiothreitol, proteinase K, and 2% sodium dodecylsulfate in order to extract DNA from the digest by a complex chemical extraction method.

Also noted are certain patents, e.g., U.S. Pat. Nos. 3,986,926, 3,966,551, 3,939,040 and 3,623,950, which pertain to depilatory agents for the tanning of hides, and disclose the use of certain enzymes, including papain, in the dehairing process.

However, these and other prior art methods have proven disadvantageous for the reasons noted above and/or because they degrade the analyte probes (e.g., antibodies) of biological analytical methods, thereby preventing the use of such highly sensitive analytical techniques.

Thus, there exists a need for an analyte detection method that can rapidly and completely solubilize a certain analyte from keratinized structures of the body such as hair, fingernails, toenails and skin of a subject and which permits direct analysis of the identity of the analyte and the duration of use of the analyte in, or exposure to, a subject, without destroying the analyte of interest and/or an analyte probe of biological analytical methods.

SUMMARY OF THE INVENTION

It is an object of the invention to provide a drug and chemical detection method;

It is another object of the invention to provide a drug and chemical hair analysis method;

It is another object of the invention to provide a reliable method of solubilizing, and directly analyzing the identity of, analytes in head and body hair and other keratinized structures of the body, and, where applicable, of determining the duration and extent of exposure of the analyte in a subject;

It is yet another object of the invention to provide a hair analysis method that solubilizes an analyte from the inner core of hair without causing damage to the analyte;

It is yet another object of the invention to provide a reliable hair solubilization and direct analyte detection method that effectively permits the use of highly accurate biological analytical methods;

It is yet another object of the invention to provide a reliable hair analysis method that may be performed in a much less period of time than known hair analysis methods.

These and other objects are achieved by the novel analysis method according to the invention, which comprises preparing a mixture containing a low-redox potential compound such as dithiothreitol (DTT) or dithioerythritol (DTE), an enzyme suitable for the dissolution of keratinized structures and a sample of a keratinized structure; permitting DTT or DTE to activate the keratinized structure and/or the enzyme; permitting the enzyme to at least substantially dissolve the sample of keratinized structure to form a keratin digest solution; and subjecting a portion of the keratin digest solution to analysis to detect the identity and amount of the analyte, if present, in the keratinized structure sample.

The preferred keratinized structure is hair. The enzyme may be selected from the group consisting of peptidase, endopeptidase, and protease and preferably is papain, chymopapain, or proteinase K. In order to accelerate the process, copper, e.g., in the form of cupric sulfate, or sodium arsenite ($Na_2AsO_2$) may be added to the digest solution to deactivate excess dithiothreitol or dithioerythritol in the mixture which may interfere with various components of the mixture. Preferably, the analysis of the solubilized analyte is performed by a biological analytical method such as an immunoassay.

DETAILED DESCRIPTION OF THE INVENTION

In accordance with the present invention, a method is provided that permits the rapid and complete solubilization of a certain analyte from head or body hair or other keratinized structures of an individual who has previously been exposed to the analyte, e.g., has ingested the analyte, followed by the identification of the analyte by known analytical biological probes, such as the rapid and highly sensitive immunoassays. The solubilization of the analyte from the interior of hair is effectuated without damaging the analyte trapped within the organic matrix of the hair fiber which is to be analyzed, nor does it affect a subsequently-used probe (e.g., antibody) of a biological analytical method. The hair analysis method according to the invention also permits the detection of past use patterns in a subject over extended periods of time without performing repeated testing as is necessary in conventional analyte detection methods which measure the content of the analyte in samples of blood or urine.

More particularly, the invention comprises the rapid enzymatic digestion of the proteins making up samples of hair and other keratinized structures, followed by the effective deactivation of the enzyme and associated enzyme/substrate activator (DTT and DTE). The resultant solubilized analyte in the hair digest solution may then be analyzed by known biological analytical probes, preferably by highly sensitive protein-based analytical techniques such as immunoassay. It has been found that the amount of analyte entrapped in hair is directly proportional to the amount of analyte ingested.

In accordance with the invention, a sample of a keratinized structure, e.g., hair, is first collected from a subject suspected of having been exposed to, or having ingested, a particular analyte. Preferably, the hair sample is first washed by known methods to remove analyte or other drug or chemical which may have been deposited on the surface of the hair by external contact rather than by actual consumption. The hair sample is then subjected to treatment with particular enzymes, together with a particular enzyme/substrate activator, so as to effectuate the complete or nearly complete digestion of the organic matrix of the hair fiber, known as keratin. The subject analyte that has been "entrapped" within the organic matrix of the hair is then released into solution, or even if protein bound, the analyte is accessible to the antibody employed in protein-based analytical methods. In order to fully and accurately carry out the method according to the invention, a complete digestion of the keratinized structure is desirable.

The enzymes preferred for the digestion of the hair samples are those of the enzyme classes peptidase, endopeptidase and protease. Most active, and therefore preferred for use in the invention, are the enzymes papain, chymopapain and proteinase K.

A number of other proteases have been found to be effective in the method according to the invention at low pH values (e.g., pH 7–9), namely, protease Type IV (bacterial, from *Streptomyces caespitosus*), Type VIII (from *Bacillus subtilis*), Type XI (proteinase K, fungal, from *Tritirachium album*), Type XIV (pronase, from *Streptomyces griseus*), Type XVI (from *Bacillus subtilis*), Type XVIII (Newlase, from *Rhizopus* species), Type XIX (from *Aspergillus sojae*), Type XXI (from *Streptomyces griseus*), Type XXIV (bacterial), Type XXVII (*Nagarase*), Type III (*Prolase*) and Type XXIII (from *Aspergillus oryzae*) (all available from Sigma Chemical Co., St. Louis, MO).

As noted above, certain art-recognized procedures provide for the use of papain for use as a hair depilatory. These depilatory methods remove hair from hides and skin by softening it sufficiently so as to permit its ready removal by scraping or other mechanical means, and utilize inexpensive and less effective sulfhydryl enzyme and substrate activators such as thioglycolic acid or cysteine. These methods only partly degrade the hair and do not provide for the complete chemical digestion of the hair. A mere softening of the hair does not lead to the complete, or nearly complete, digestion of hair which is necessary in order to obtain a complete release of "entrapped" analyte. Moreover, the sulfhydryl enzyme activators used in these depilatory methods are also harmful to certain biological analyte probes such as antibodies.

In contrast to these depilatory methods, the method of the present invention utilizes dithiothreitol ("DTT", or 2,3-dihydroxybutane-1,4-dithiol) or its isomer dithioerythritol ("DTE", or 2,3 dihydroxybutane-1,4-dithiol) as the substrate and sulfhydryl-enzyme activating agent. surprisingly, it has been found that DTT and DTE produce a highly active enzyme capable of digesting hair within a relatively short period of time, e.g., about three hours, resulting in the release of the analyte into the hair digest solution. This high activity of the enzyme has been found to be due, at least in part, to the activation of the keratinized structure substrate itself by DTT and DTE, presumably by the action of DTT and DTE in opening up disulfide bonds in the keratinized structure, which facilitates enzymatic attack.

Once the protein of the keratinized structure has been completely or at least substantially dissolved, thereby releasing the analyte into the solution mixture, it has been found to be necessary to deactivate the enzyme and the enzyme/substrate activator(s) in order to subject the analyte to biological analytical probes such as antibodies, since the enzyme and enzyme/substrate activator(s), as noted above, can interfere with the structural integrity of protein substances involved in the analytical method.

The task of deactivating the sulfhydryl-dependent enzymes such as papain has proven difficult since after the hair digestion step, the enzymes are "buried" in a "sea" of sulfhydryl groups belonging to the released hair proteins and enzyme/substrate activating agents. Known sulfhydryl blocking agents are ineffective in deactivating the enzymes, since the known sulfhydryl blockers tend to bind to the degraded hair proteins and DTT or DTE and not necessarily to the enzyme sulfhydryl sites critical for blocking the activity of the enzymes. Thus, it is not possible to effectively utilize the protein-based analytical methods if the enzyme sulfydryl sites are still active.

Thus, it was surprisingly discovered that DTT and DTE act not only to activate enzymes and/or the keratinized structure substrate causing unexpectedly high hair digestion activity, but that they also may act to deactivate the enzyme by a direct or indirect (enzyme self-deactivation) mechanism after the enzyme effectuates the complete, or nearly complete, digestion of the hair protein. Typically, the enzyme deactivation occurs within about four to five hours after exposure of the DTT or DTE to the enzyme, which is a sufficient amount of time for the enzyme to effectuate the digestion of the hair sample. Once the enzyme has been deactivated, it has been found that the enzyme cannot be reactivated or regenerated by exposure to fresh DTT or DTE.

Deactivation of at least certain of the non-sulfhydryl dependent proteases, e.g., proteinase K, by its inhibitor, phenylmethyl sulfonyl chloride, is generally not required since the enzyme has not been found to be active against the antibodies used in protein based immmunoassay techniques.

It has also been found that active DTT and DTE present in the hair digest solution constitute a hazard to the structure and activity of other proteins to which it is exposed, e.g., antibodies utilized in radioimmunoassay. Thus, it was a further surprising result that DTT or DTE in the reaction mixture may not only act to deactivate the enzyme, but itself becomes deactivated in the digest solution without the introduction of an inhibitor. Typically, the spontaneous deactivation of DTT or DTE will occur after the hair sample has been digested but less than about 14 hours after its first exposure to the enzyme, depending on the various concentrations and amounts of the enzyme and DTT or DTE utilized, the pH, temperature, amount of hair sample, etc.

Thus, in accordance with the method of the invention, complete hair digestion can be carried out in a relatively short period of time, e.g., overnight, and the hair digest solution, which includes the released analyte of interest, can be directly subjected, effectively and accurately, to protein-based ligand assay analysis methods the next morning. Typically, the entire method, from the washing of hair samples to the identification of the analyte, should take no longer than about 16–20 hours. Little or no intervention by the individual performing the method is needed to release the analyte from the hair sample once the enzyme and DTT or DTE come into contact with the hair sample.

Alternatively, it has been discovered that the addition of copper, preferably in the form of cupric sulfate or other similar compound, to the sulfhydryl group-rich hair digest solution acts to more rapidly deactivate the sulfhydryl groups of DTT or DTE. Thus, the addition of low amounts of the cupric sulfate to the hair digest mixture after digestion of the hair sample and the deactivation of the enzyme by DTT or DTE significantly accelerates the time in which the hair digest mixture can be subjected to the analysis method since it is not necessary to wait for the deactivation of DTT or DTE, which typically occurs less than about fourteen hours after its addition to the digest solution. Typically, about 100 microliters of cupric sulfate (10 mg/ml) is added to 1 ml of hair digest solution about 4 to 5 hours after contacting the enzyme and (DTT or DTE) with the hair sample so as to permit the enzyme sufficient time to dissolve the hair sample.

Similarly, sodium arsenite ($NaAsO_2$) may be utilized in the invention to remove residual DTT or DTE by formation of a precipitable compound. Typically, 100 microliters of a 100 mg/ml solution of sodium arsenite is added to 1 ml of hair digest solution to effectuate the deactivation of DTT and DTE.

Once the rapid and effective dissolution of hair for the purpose of releasing entrapped analyte is effectuated as described above, the analyte mixture may then be subjected to direct analysis by art recognized protein-based analytical methods such as radioimmunoassay ("RIA"). Such methods are preferred for use in the invention because RIA and related immuno- or ligand assays are currently the only known mass production procedures having the required sensitivity and convenience for measuring the low concentrations of analytes contained in hair samples. The use of these methods is preferred because only about 0.5 to 1.0 mg. of hair is necessary for analysis by RIA and other protein-based analytical methods. Indeed, for certain drugs-of-abuse, it has been found that analysis by the method according to the invention can be effectively performed on as little as one or two hairs about one inch in length.

Other analytical methods may be utilized in place of the protein-based analytical methods, including instrumental means such as chromatography, mass spectrometry, etc. Because these methods are not protein-based, the steps of deactivation of the enzyme and DTT or DTE is not necessary when using non-protein-based analytical techniques. However, the speed and gentleness of the extraction method according to the invention and the ability to quantitate the extraction efficiency through the inclusion of a "spike", i.e., the inclusion of a known amount of analyte, makes the presently disclosed digestion method also the method of choice for instrumental analysis methods such as gas chromatography and mass spectrometry.

The method according to the invention has been found to be effective in detecting the use and prior use of drugs of abuse such as cocaine, morphine/heroin, marijuana, phencyclidine or "PCP", methaqualone and methamphetamine. Moreover, the method according to the invention has been found to be effective in determining prior usage of prescription drugs such as digoxin and amphetamines and toxic chemicals such as nicotine. It is contemplated that any organic analyte present in the bloodstream of an individual which is transferred to the hair during its synthesis can be extracted and analyzed in accordance with the method of the invention.

In carrying out the method, it is preferred that an aqueous solution of about 110 mg DTT or DTE/10 ml water be used, although concentrations of DTT or DTE of about 50–200 mg/10 ml water are effective in the method. It is preferred that the weight ratio of DTT or DTE to papain or chymopapain be about 110:2 [when enzyme purity is 16–40 BAEE units/mg protein], although efficacious results have been observed at weight ratios of DTT or DTE to papain or chymopapain ranging between about 110:1 to about 110:4. With respect to proteinase K and other proteases, it is preferred that the weight ratio of DTT or DTE to proteinase K (or other proteases) be about 1200:1 (when enzyme purity is 10–20 units per mg. protein), although weight ratios of 1200:0.5 to about 1200:2 will also be effective.

The concentration of hair protein is preferably kept constant at about 10 mg hair /cc of digest solution so as to prevent variable matrix effects in a subsequently utilized protein-based analytical method.

It is preferred that the enzymatic digestion of hair, according to the method of the invention, be conducted at low temperatures and near neutral pH. In this regard, it is preferred to perform the method when papain, chymopapain or other sulfhydryl dependent enzyme is utilized as the enzyme, at a temperature of between about 20° C. and 40° C., and at a pH between about pH 8.8 and 10.5. Preferably, the pH of the method is between about 8.8 and 9.5. In a most preferred embodiment, the temperature is about 37° C. and the pH about 9.1.

When proteinase K or other proteases are utilized as the enzyme, it is preferred to perform the method between about 20 and 40 degrees centigrade and at a pH between about 7 and 9. In the most preferred embodiment, the temperature is about 37 degrees centigrade and the pH about 7.0; under these conditions, the risk of damaging a particular analyte is at a minimum. Other enzymes which dissolve hair under neutral or acid conditions include: Protease Type XIV (Pronase), Type III (Prolase), Type IV, Type VIII, Type XVI, Type XVIII, Type XIX, Type XXIV, Type XXVII (Nagarse), Type XXVIII, Type XXI and Type XXIII.

Under certain circumstances, it is advantageous to perform the method according to the invention at a lower than usual pH in order to preserve the chemical structure of the analyte or to simplify the performance of the method. As stated above, the digestion of hair will occur at a pH between about 8.8 and 10.5 when a sulfhydryl dependent enzyme (e.g., papain) is utilized and between 7 and 9 when a protease (e.g., Proteinase K) is utilized. At any pH in either of these ranges, however, certain analytes may become unstable or hydrolyze to a different form, which may impact on the measure of both quantity and quality of the analyte in the subsequent analysis step.

For example, cocaine will hydrolyze to benzoylecgonine at a pH above about 6.6 and a temperature of 37° C. Thus, injected cocaine naturally will hydrolyze to benzoylecgonine in the blood and eventually end up entrapped in hair as benzoylecogonine, and the digestion of hair from a cocaine user will lead to the release of the benzoylecgonine from the hair into solution thereby permitting a positive identification of cocaine ingestion by immunoassay. The method of the invention thus actually measures the amount of benzoylecgonine, rather than the amount of cocaine, that has been incorporated into the hair from blood. However, a problem may arise if there is inadequate washing of the hair sample prior to digestion if the digestion is performed at a pH greater than about 6.6 in that a false positive result may be obtained if the individual being tested was exposed to atmospheric cocaine that has settled on the surface of the inadequately washed hair sample.

Thus, in the case of certain analytes such as cocaine which may be chemically altered by a higher pH, it is desirable to perform the method of the invention at a pH which avoids hydrolysis or other chemical reaction of atmospheric analyte which inadvertently has ended up in the digest solution. In the case of cocaine, performance of the method at a pH below about 6.6 at 37° C. will ensure that the benzoylecgonine in the sample is directly related to the amount of cocaine ingested by the subject.

According to the invention it has been found that certain biological detergent compounds useful for solubilizing biological membrane components aid in the digestion of hair at a relatively low pH while not interfering with enzymatic activity or the antibody-antigen reaction which will influence the sensitivity of the immunoassay. This is surprising and unexpected since other biological detergents have been found to be unsuitable for use in the invention because they are ineffective in aiding digestion at the desired low pH, they deactivate proteinase K or other hair protein digestion enzymes and/or they impact on the binding of the analyte by the antibody thereby drastically reducing the sensitivity of the immunoassay. See, e.g., Higuchi, R. et al., "DNA Typing From Single Hairs", *Nature*, 332:543–546, 1988.

The biological detergents together with an appropriate enzyme (e.g., protease and sulfhydryl enzymes) and activator (e.g., DTT and DTE), are effective in aiding the digestion of the hair sample at a lowered pH in the range of about 6.2 and 8. Certain of the biological detergents described herein are effective in the invention at a pH as low as about 5.8.

The protease enzymes (e.g., proteinase K) are preferred for use with the biological detergents disclosed herein. The biological detergents also effectively may be used together with the sulfhydryl enzymes, e.g., papain, to effectuate digestion of a hair sample at a lower pH.

The biological detergents found to be useful in the invention include the bile acid detergents, such as glycocholic acid, cholic acid, taurocholic acid, deoxycholic acid, glycodeoxycholic acid, taurodeoxycholic acid and salts thereof, including sodium salts. Other detergents effective for use in the invention are sulfo-betaines, such as the Zwittergents®, and betaines, such as Empigen BB (N-dodecyl-N,N dimethylglycine) (all available from Calbiochem Corp., La Jolla, Calif.).

Still other detergents which are useful in aiding the digestion of hair according to the invention at a relatively lower pH are the alkylglucosides, including hexyl-B-D-glucopyranoside, heptyl-B-D-glucopyranoside, octyl-B-D-glucopyranoside, nonyl-B-D-glucopyranoside, decyl-B-D-glucopyranoside, dodecyl-B-D-maltoside and octyl-B-D-thioglucopyranoside (OSGP). Mixtures of alkylglucosides, such as the product ELUGENT (Calbiochem), are also effective.

Particularly preferred for use in the invention are the bile acids cholic acid and glycocholic acid which aid in the digestion of hair at a pH in the range of about 6.3–8. The deoxycholates such as deoxycholic acid and glycodeoxycholic acid are effective in aiding in the digestion of hair at a pH above about 7.

As discussed above, the hydrolysis of cocaine occurs at a pH of about 6.6 and above at 37° C. To avoid hydrolysis of cocaine to benzoylecgonine, the hair digestion preferably is performed at a pH in the range of about 6.2–6.5. To this end, the cholate detergents are preferred over the deoxycholate detergents which effectuate the digestion at a somewhat higher pH.

Of the sulfo-betaine detergents manufactured by Calbiochem Corp. of La Jolla, Calif., Zwittergent® SB3-14 (CAS Registry No. 14933-09-6, N-tetradecylsulfobetaine or 3-(dodecyldimethylammonio) propane-1-sulfonate) is preferred. Digestion of hair using the Zwittergent® sulfobetaine detergents typically occurs at about pH 6.3 at 37° C. Zwittergents® are of the class of detergents known as sulfo-betaines having the general structure:

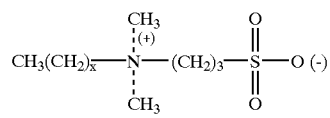

wherein x may be any number which provides an effective biological detergent. Preferred are those compounds wherein x is in the range of 7–16. Most preferred is the detergent when x is 14. Other Zwittergent® sulfo-betaine detergents useful in the invention include:

1. Zwittergent® SB3-08 wherein x=7 [N-octyl sulfo betaine or 3-(Octyldimethylammonio) propane-1-sulfonate] [CAS Registry # 15178-76-4].
2. Zwittergent® SB3-10 wherein x=9 [N-D-dodecylsulfobetaine or 3-(dodecyldimethylammonio) propane-1-sulfonate] [CAS Registry # 15163-36-7].
3. Zwittergent® SB3-12 wherein x=11[N-dodecylsulfobetaine or 3-(Dodecyldimethylammonio) propane-1-sulfonate] [CAS Registry #14933-09-6].
4. Zwittergent® SB3-14 wherein x=13 [N-tetradecylsulfobetaine or 3-(Dodecyldimethylammonio) propane-1-sulfonate] [CAS # 14933-09-6].
5. Zwittergent® SB3-16 wherein x=15 [N-Hexadecylsulfobetaine or 3-(Hexadecyldimethylammonio) propane-1-sulfonate] [CAS #2281-11-0] The bile acid detergents and Calbiochem Zwittergents® SB3-8, SB-10, SB3-12, SB3-14 and SB3-16 (x in the range of 7–16) are preferred in effectuating the digestion of hair at a relatively lower pH which is desirable in methamphetamine, PCP and opiates assays. The cholate and Calbiochem Zwittergents® are preferred for use in the cocaine assay. The cholate and deoxycholate detergents are preferred for use in marijuana screening assays.

In practice, the biological detergent is mixed with the aqueous digest solution of the activator such as DTT (or DTE) and the enzyme (preferably proteinase K) prior to contact of the solution with the hair sample at a preferred temperature range of about 30–40° C. as described herein. Typically, about 1–2 mg of biological detergent is added to about 1 cc of digest solution.

In contrast to other available analyte detection methods such as urine and blood analysis, the method in accordance with the invention permits detection of exposure to an analyte over a period of time, and is therefore quite beneficial in detecting chronic drug use. Since hair is known to grow at a rate of about 0.3–0.4 mm/day or about 1.0–1.3 cm/month, it is possible to measure consumption or exposure as far back as the hair length permits by evaluating snippets of hair of various lengths, and the use of highly sensitive protein-based analytical methods permits analysis of small samples of analyte contained in the small snippets of hair.

Through sectional analysis, the method of the invention provides a relatively permanent record and evidence of a pattern of drug use, or the prior ingestion of other substances, for periods ranging from several days to months or even years after last use. The history of such exposure can be made as detailed as desired by analyzing suitably short sections of hair representing different periods of growth. In this way, prior usage over time, and the extent of such use, can be determined.

Although the use of head hair is preferred for use in the invention due to its length and accessibility, it is possible to utilize any other body hair in the method of the invention. Thus, it is not practically possible to avoid testing by the method of the invention by shaving one's head.

However, treatments such as perming and dyeing may increase the rate of dissolution of hair subjected to the method according to the invention. In some cases, some analyte may be lost prior to performing the procedure due to such treatments. When the subject hair has been so altered, an increase in digestion rate is evident and an appropriate correction factor may be applied based upon known rates of normal hair dissolution.

Certain other cosmetic agents, such as certain relaxing agents, may cause hair to become resistant to digestion. Such resistance may be overcome by increasing the quantity of enzyme to be used. Preferably, proteinase K is utilized as the enzyme when such resistance to digestion is encountered.

Alternatively, when it is not possible to make use of body hair or in some instance when the use of hair is not desirable, the use of other keratinized tissue such as fingernails and toenails may be used in the invention. In this regard, the effective ratio of DTT or DTE to enzyme needed to dissolve fingernails and toenails in order to release the analyte is about the same as for use with hair, as discussed above. Once the fingernail or toenail samples are dissolved in accordance with the method described herein, the released analyte may be analyzed by a desired analytical method.

In another aspect of the invention, it has been surprisingly discovered that melanin granules contained in hair can be dissolved by the combined action of the enzyme (preferably papain), DTT or DTE and ethylene diamine tetraacetic acid (EDTA), the latter at a concentration of about 5 mg EDTA/ml of digest solution. Since certain analytes or drugs of abuse such as PCP have been discovered to accumulate in these granules, dissolution of the granules, which are present in the digest solution of hair, can be effectuated and the analyte contained in the granule identified.

In accordance with this aspect of the invention, a hair digest solution is obtained as described above, and the melanin granules recovered from the hair digest solution, e.g., by centrifugation. The melanin granules are then contacted with EDTA, the enzyme and DTT or DTE to release the analyte from the melanin granules, and the analyte analyzed by the methods described above.

The benefits to be obtained from use of the method according to the invention are many. The method provides a prompt and accurate diagnosis of prior exposure to a particular analyte. The subject hair and keratinized structure analysis method can provide a record of consumption, or non-consumption, over very long periods of time. Guess work regarding the true significance of one blood or urine analysis will be eliminated. Hair collection is less intrusive and less physically repulsive than blood or urine collection, and samples cannot be altered or substituted, nor can detection be evaded by short term abstention or "flushing" (excessive fluid intake) prior to a scheduled testing, e.g., pre-employment test or annual physical examination. Samples may be stored indefinitely without refrigeration.

The methods according to the invention, useful for the digestion of keratinized structures, e.g., hair, can also be used to ascertain the presence and structure of naturally occurring components of hair such as DNA.

The following examples illustrate certain aspects of the invention but they do not limit the invention as set forth in the specification and claims.

EXAMPLE 1

Extraction of Cocaine From Hair Sample 10 mg of hair was removed from a subject suspected of being a cocaine addict and washed by shaking in water at 37° C. for 30 minutes. To 10 ml. of distilled water, 110 mg. of dithiothreitol (2,3-dihydroxybutane-1,4-dithiol, Cleland's reagent, obtained from Sigma Chemical Co., St. Louis, MO.), was added. The pH of the solution was adjusted to pH 9.1 with 15% potassium hydroxide added dropwise with stirring of the DTT solution. Stirring was continued while adding 80 microliters of Type III papain solution (papainase EC 3.4.22.2) (obtained from Sigma Chemical Co., 16–40 BAEE units activity per mg. protein). The enzyme solution was at a concentration of 30 mg of enzyme protein/ml of water, where 1 mg of enzyme protein has an activity of 16–40 BAEE units [one BAEE unit will hydrolyze 1.0 micromole of sodium benzoyl-L-arginine ethylester at pH 6.2 at 25° C.].

To 1 ml of this solution was added the 10 mg hair sample in a 13×75 mm polycarbonate test tube. The solution was incubated in a 37° C. water bath with shaking for 2 hours, and the solution was allowed to stand overnight at 37° C. without shaking. The solution containing the dissolved hair sample was centrifuged at 2,000 rpm [Damon IEC model CRU 5,000 centrifuge] to remove the melanin granules. To 1 cc of the hair digest solution was added 200 microliters of a 1 molar phosphate buffer, pH 5.5.

100 microliters of this solution was assayed by RIA for the presence of cocaine [benzoylecgonine equivalent, or "BEE"]. RIA analysis revealed 83.6 nanograms BEE/10 mg of hair.

EXAMPLE 2
Addition of Dithioerythritol

The hair sample of Example 1 was analyzed using the digestion and assay procedure set forth in Example 1, except for the replacement of dithiothreitol (DTT) by dithioerythritol (DTE). The sample was assayed by RIA, which revealed 82 nanograms cocaine (BEE) per 10 mg of hair.

EXAMPLE 3
Addition of Cupric Sulfate

After digesting the hair sample in the water bath for four hours, 100 microliters of a 10 mg/ml cupric sulfate solution was added to 1 ml of the hair digest solution prepared as set forth in Example 1. The solution was shaken at 37° C. for about 30 minutes prior to the addition of phosphate buffer and assay by RIA. One hundred microliters of the hair digest solution was subjected to RIA analysis, which revealed 85.0 nanograms of cocaine (BEE)/10 mg of hair.

EXAMPLE 4
Addition of Sodium Arsenite

After digesting the hair sample in the water bath for four hours, 100 microliters of a 100 mg/ml sodium arsenite solution was added to 1.0 ml of the hair digest solution prepared as set forth in Example 1. The solution was shaken at 37° C. for 30 minutes. 200 microliters of 1M, pH 6.5, phosphate buffer was added prior to assay by RIA. One hundred microliters of the hair digest solution was subjected to RIA analysis, which revealed 82 nanograms of cocaine (BEE) per 10 mg of hair.

EXAMPLE 5
Substrate Activation By Dithiothreitol (DTT)

10 mg of hair were exposed to 11 mg of DTT at pH 9.1 for a period of 20 hours. The DTT solution was removed and replaced with DTT and papain as in EXAMPLE 1. The hair specimen dissolved within 10 minutes as compared to within one hour for a control specimen not pretreated with DTT and digested as in EXAMPLE 1, thereby demonstrating that DTT activated not only the sulfhydryl-dependent enzyme, papain, but the enzyme substrate, hair, as well.

EXAMPLE 6
Digestion and Analysis of Hair Using Proteinase-K mg of hair was removed from a subject suspected of being a cocaine user and washed by shaking in water at 37 degrees centigrade for 60 minutes. To 10 ml of 0.05 M TRIS buffer, pH 7.0, 60 mg of dithiothreitol (DTT) and 20 mg sodium dodecyl sulfate (lauryl sulfate) was added. The pH of the solution was checked to ensure the solution was buffered at a pH 7.0. To this solution was added 0.5 mg proteinase K [Protease Type XI, from Tritirachium album, obtained from Sigma Chemical Co.; 1 mg of enzyme protein has an activity of 10–20 units; one unit will hydrolyze casein to produce color equivalent to 1.0 $\mu$mole (181 ug) of tyrosine per minute at pH 7.5 at 37 degrees centigrade (color by Folin-Ciocalteu reagent)].

To 1 ml of this solution was added the 10 mg hair sample in a 13×75 mm polycarbonate test tube. The solution was incubated in a 37° C. water bath with shaking for 1 hour and allowed to stand overnight at 37° C. without shaking. The solution containing the dissolved hair sample was centrifuged at 2,000 RPM to remove the melanin granules. To 1 cc of the hair digest solution was added 100 microliters of cupric sulfate penahydrate (10 mg/ml), and this solution was shaken at 37° C. for 30 minutes. 200 $\mu$l of 1 M phosphate buffer, pH 7.0, was then added.

100 microliters of this solution was assayed by RIA for the presence of cocaine (benzoylecgonine equivalents, or BEE). RIA analysis revealed 31.2 nanograms BEE/10 mg of hair.

EXAMPLE 7
Role of Sulfhydryl Compounds in the Activation of Hair for Proteinase K Digestion 10 mg of hair was incubated in a solution identical to that described in EXAMPLE 6 except that DTT was omitted. No digestion of hair occurred during 24 hours of enzyme exposure, thereby demonstrating the need for the activation of the hair sample by the substrate activator, DTT.

EXAMPLE 8
Dissolution of Fingernails

A 10 mg. sample of fingernail clippings was obtained from a subject, and subjected to a detergent wash. 220 mg of DTT was added to 10 ml of water in a test tube and the pH adjusted to pH 9.1 as in Example 1. A papain suspension, 160 microliters, was then added. 1.0 ml of this solution was then added in a test tube to 10 mg of fingernail clippings and shaken at 37° C. for a period of 24 hours until dissolution occurred. The digest solution was then analyzed by RIA as previously described.

EXAMPLE 9
Performance of Sectional Analysis

A hair sample, about 6 cm in length, was obtained from an individual suspected of being a heroin addict. The samples were carefully sectioned into three 2 cm sections, with corresponding sections added to three separate test tubes and washed. The hair samples were subjected to the process described in Example 1, except that chymopapain (EC 3.4.22.6) was used in place of papain as the enzyme. The samples were agitated overnight as previously described.

RIA analysis revealed morphine content in the three sections of 13.5, 5.7 and 0 nanograms/10 mg hair.

EXAMPLE 10
Dissolution of Digestion-Resistant Hair

Ten milligrams of hair which had been treated with relaxer was incubated overnight in the solution digest described in Example 6. The hair sample did not dissolve in the usual 20-hour period. A greater and additional amount of proteinase K, i.e., 1 mg, was then added to the partially digested sample. The sample then dissolved within the next 24 hours. The digest was centrifuged and 100 $\mu$l $CuSO_4$ solution (10 mg/ml) was added to 1 ml of the supernatant which was then shaken at 37 degrees centigrade for 30 minutes. 200 $\mu$l of 1 M phosphate buffer pH 7 was added. Due to the high amount of proteinase K in the resulting digest, 20 $\mu$l of the proteinase inhibitor phenylmethyl sulfonyl chloride in ethanol was added to the digest prior to assay by RIA.

RIA analysis revealed 7.4 ng cocaine (BE)/10 mg hair.

EXAMPLE 11
Digestion And Analysis of Hair Using Proteinase K and Cholic Acid Detergent Separate samples of 10 mg of normal hair and 10 mg of hair containing the cocaine metabolite benzoylecgonine (BEE) were collected and placed in separate 12×75 mm polycarbonate tubes. One ml of the following solution was added to the hair in each of the tubes: 0.5M Tris buffer (pH 6.5 at room temperature) containing one ml 2 U Proteinase K, 20 mg cholic acid (sodium salt) and 60 mg dithiothreitol. The mixtures were shaken 16 hours at 37° C. After 16 hours, the samples were centrifuged at 3,000 RPM for 20 minutes. To 0.9 ml of the supernatant removed after centrifugation was added 10 $\mu$l of phenylmethylsulfonyl fluoride (6% in Ethanol). This was mixed, followed by the addition of 90 ul $CuSO_4.5H_2O$ (10 gm/liter) to each solution. This mixture was shaken at 37° C. for 30 minutes. 100 μl of this mixture was then assayed by RIA. Equivalent solutions as described but containing no cholic acid detergent and no hair protein were also assayed. The results were as follows:

A. Sample of hair protein not containing cholic acid or BEE: 14,686 cpm (counts per minutes on gamma counter) ($B_o$).

Sample of hair protein containing 0.14 ng BEE and no cholic acid: 11,128 cpm (B), or a $B/B_o$ of 76% (indicating the presence of BEE).

B. Sample of hair containing cholic acid but no BEE: 12,048 cpm ($B_o$)

Sample of hair containing 0.14 ng BEE and cholic acid: 8,602 cpm (B), or a $B/B_o$ of 71% (indicating presence of BEE)

The similarity of the resulting $B/B_o$'s (76% and 71%) with and without cholic acid indicate that cholic acid did not interfere with the assay for cocaine or benzoylecgonine.

EXAMPLE 12

Digestion And Analysis of Hair Using Proteinase K and Octyl-B-D-glucopyranoside

A sample of 10 mg of normal hair was collected and placed in a 12×75 mm polycarbonate tube. One ml of the following solution was added to the hair in the tube: 0.5M Tris buffer (pH 6.5 at room temperature) containing 2 U Proteinase K, 2 mg octyl-B-D-glucopyranoside and 60 mg dithiothreitol. The mixture was shaken 16 hours at 37° C. After 16 hours, the sample was centrifuged at 3,000 RPM for 20 minutes. To 0.9 ml of the supernatant removed after centrifugation was added 10 μl of phenylmethylsulfonyl fluoride (6% in Ethanol). This was mixed, followed by the addition of 90 ul $CuSO_4.5H_2O$ (10 gm/liter) to each solution. This mixture was shaken at 37° C. for 30 minutes. 100 μl of this mixture was then assayed by RIA. Equivalent solutions as described but containing 2 mg cholic acid instead of octyl-B-D-glucopyrandoside were also assayed. The results were as follows:

A. Sample of hair protein containing cholic acid: 11,911 cpm (counts per minutes on gamma counter) ($B_o$).

Sample of hair protein containing octyl-B-D-glycopyranoside and no cholic acid: 12,318 cpm ($B_o$).

The similarity of the resulting $B_o$ values with and without cholic acid indicate that the assay for cocaine, or benzoylecgonine, is not affected by the use of octyl-B-D-glycopyranoside as detergent.

EXAMPLE 13

Digestion And Analysis of Hair Using Proteinase K and Octyl-B-D-Thioglucopyranoside Detergent A sample of 10 mg of normal hair was collected and placed in a 12×75 mm polycarbonate tube. One ml of the following solution was added to the hair in the tube: 0.5M Tris buffer (pH 6.5 at room temperature) containing 2 U Proteinase K, 2 mg octyl-B-D-thioglucopyranoside and 60 mg dithiothreitol. The mixtures were shaken 16 hours at 37° C. After 16 hours, the samples were centrifuged at 3,000 RPM for 20 minutes. To 0.9 ml of the supernatant removed after centrifugation was added 10 μl of phenylmethylsulfonyl fluoride (6% in Ethanol). This was mixed, followed by the addition of 90 ul $CuSO_4.5H_2O$ (10 gm/liter) to each solution. This mixture was shaken at 37° C. for 30 minutes. 100 μl of this mixture was then assayed by RIA. Equivalent solutions as described but containing as the detergent cholic acid were also assayed. The results were as follows:

A. Samples of hair protein containing cholic acid: 11,911 cpm (counts per minutes on gamma counter)

Sample of hair protein containing octyl-B-D-thioglucopyranoside: 12,888 cpm.

The results indicated that the assay is not affected by the use of octyl-B-D-thioglucopyranoside as detergent.

EXAMPLE 14

Digestion And Analysis of Hair Using Proteinase K and Empigen BB (N-dodecyl-N,N dimethylglycine) Detergent 10 mg of normal hair was collected and placed in a 12×75 mm polycarbonate tube. One ml of the following solution was added to the hair in the tube: 0.5M Tris buffer (pH 6.5 at room temperature) containing 2 U Proteinase K, 2 mg EMPIGEN BB of Calbiochem Biochemicals, and 60 mg dithiothreitol. The mixture was shaken 16 hours at 37° C. After 16 hours, the samples were centrifuged at 3,000 RPM for 20 minutes. To 0.9 ml of supernatant removed after centrifugation was added 10 μl of phenylmethylsulfonyl fluoride (6% in ETOH). This was mixed, followed by the addition of 90 μl $CuSO_4.5H_2O$ (10 gm/liter) to the solution. This mixture was shaken at 37° C. for 30 minutes. 100 μl of this mixture was then assayed by RIA. An equivalent solution as described but containing 2 mg cholic acid in place of EMPIGEN BB was also prepared and assayed. The results were as follows:

A. Sample of hair containing cholic acid: 11,911 cpm

B. Sample of hair containing EMPIGEN BB: 13,000 cpm.

The results indicated that the assay is not affected by the use of N-dodecyl-N,N-dimethylglycine as detergent.

EXAMPLE 15

Digestion And Analysis of Hair Using Proteinase K and Cholic Acid Detergent of Lower Concentration (2 mg/ml)

Separate samples of 10 mg of normal hair and 10 mg of hair containing the cocaine metabolite benzoylecgonine (BE) were collected and placed in separate 12×75 mm polycarbonate tubes. One ml of the following solution was added to the hair in each of the tubes: 0.5M Bis-Tris buffer (pH 6.5 at room temperature) containing in one ml 2 U Proteinase K, 2 mg cholic acid (sodium salt), and 60 mg dithiothreitol. The mixture was shaken 16 hours at 37° C. After 16 hours, the samples were centrifuged at 3,000 RPM for 20 minutes. To 0.9 ml of supernatant removed after centrifugation was added 10 μl of phenylmethylsulfonyl fluoride (6% in Ethanol). This was mixed, followed by the addition of 90 μl CuSO. $5H_2O$ (10 gm/liter) to the solution. This mixture was shaken at 37° C. for 30 minutes. 100 ul of this mixture was then assayed by RIA. The results were as follows:

A. Sample of hair having cholic acid but no BEE: 14,430 cpm ($B_o$)

B. Sample of hair containing 0.14 ng BEE and cholic acid: 10,822 cpm (B), or a $B/B_o$ of 75% which is consistent with the $B/B_o$ values of Example 11.

EXAMPLE 16

Digestion And Analysis of Hair Using Proteinase K and Zwittergent® 3–12 Detergent 10 mg of normal hair and 10 mg of hair containing the cocaine metabolite benzoylecgonine (BE) were collected and placed in separate 12×75 mm polycarbonate tubes. One ml of the following solution was added to the hair in each of the tubes: 0.5M Tris buffer (pH 6.5 at room temperature) containing in one ml 2 U Proteinase K, 2 mg Zwittergent® 3-14 of Calbiochem Biochemicals, and 60 mg dithiothreitol.

The mixture was shaken 16 hours at 37° C. After 16 hours, the samples were centrifuged at 3,000 RPM for 20 minutes. To 0.9 ml of supernatant removed after centrifugation was added 10 µl of phenylmethylsulfonyl fluoride (6% in ETOH). This was mixed, followed by the addition of 90 µl $CuSO_4.5H_2O$(10 gm/liter) to the solution. This mixture was shaken at 37° C. for 30 minutes. 100 ul of this mixture was then assayed by RIA. The results were as follows:

A. Sample of hair containing Zwittergent® Z3-14 but no BEE: 14,148 cpm ($B_o$)

B. Sample of hair containing 0.14 ng BEE and Zwittergent® 3-14: 10,326 cpm (B), or a $B/B_o$ of 73%

The B/Bo value was compared with the B/Bo values of Examples 11 and 12, which indicated that the addition of Zwittergent® 3-14 to the digest solution did not interfere with the assay for cocaine or benzoylecgonine.

While there have been described what are presently believed to be preferred embodiments of the invention, it will be apparent to one skilled in the art that numerous changes can be made in the ingredients, conditions and proportions set forth in the foregoing embodiments without departing from the invention as described herein and as defined in the appended claims.

what is claimed is:

1. A method for the identification of marijuana, cocaine, phencyclidine, methamphetamine and opiates from the bloodstream of a subject which becomes embedded in a keratinized structure of the subject which comprises:
   (a) preparing a mixture comprising a protease suitable for the digestion of keratin, an agent selected from the group consisting of dithiothreitol and dithioerythritol, a biological detergent selected from the group consisting of cholate, deoxycholate, cholic acid, deoxycholic acid, octyl-B-D-glucopyranoside and octyl-B-D-thioglucopyranoside and a sample of keratinized structure; the amounts of said protease, agent and detergent being sufficient to effectuate the digestion of the sample;
   (b) permitting the digestion of the sample to form a keratin digest solution;
   (c) ensuring that the protease and the agent will not interfere with the accuracy of an immunoassay method performed on the digest solution; and
   (d) subjecting a portion of the keratin digest solution to analysis by immunoassay.

2. The method according to claim 1 wherein the keratinized structure is hair.

3. The method according to claim 1 further comprising the step of adding cupric sulfate to the solution after the keratinized structure has been digested and before the keratin digest solution is subjected to analysis in an amount sufficient to deactivate the agent such that the amount of time necessary for the deactivation of the agent is decreased.

4. A method for the detection and identification of cocaine, opiates, phencyclidine and methamphetamine from the bloodstream of a subject which becomes embedded in the hair of a subject which comprises:
   (a) preparing a mixture comprising an agent selected from the group consisting of dithiothreitol and dithioerythritol, a protease suitable for the digestion of hair, a bile acid detergent, and a sample of hair; the amounts of said protease, agent and detergent being sufficient to effectuate the digestion of the sample;
   (b) permitting the digestion of the sample of hair to form a hair digest solution;
   (c) ensuring that said agent and said protease will not interfere with the accuracy of an immunoassay method performed on the digest solution; and
   (d) subjecting a portion of the hair digest solution to analysis by immunoassay.

5. A method for the identification of cocaine, phencyclidine, methamphetamine and opiates from the bloodstream of a subject which becomes embedded in the hair of the subject which comprises:
   (a) preparing a mixture comprising an agent selected from the group consisting of dithiothreitol and dithioerythritol, a protease suitable for the digestion of hair, a biological detergent selected from the group consisting of an alkylglucoside and mixtures of alkylglucosides and a sample of hair; the amounts of said protease, agent and detergent being sufficient to effectuate the digestion of the sample;
   (b) permitting the digestion of the sample of hair to form a hair digest solution;
   (c) ensuring that said agent and said protease will not interfere with the accuracy of an immunoassay method performed on the digest solution; and
   (d) subjecting a portion of the hair digest solution to analysis by an immunoassay.

6. The method according to claim 5 further comprising the step of adding cupric sulfate to the solution after the hair sample has been digested and before the hair digest solution is subjected to direct analysis in an amount sufficient to deactivate the agent such that the time necessary for the deactivation of the agent is decreased.

7. The method according to claim 5 wherein the alkylglucoside is selected from the group consisting of octyl-B-D-glucopyranoside, octyl-B-D-thioglucopyranoside, nonyl-B-D-glucopyranoside, decyl-B-D-glucopyranoside, dodecyl-B-D-maltoside, hexyl-B-D-glucopyranoside and heptyl-B-D-glucopyranoside.

8. A method for the identification of cocaine, phencyclidine, methamphetamine and opiates from the bloodstream of a subject which becomes embedded in the hair of the subject which comprises:
   (a) preparing a mixture comprising an agent selected from the group consisting of dithiothreitol and dithioerythritol, a protease suitable for the digestion of hair, a detergent selected from the group consisting of sulfobetaines and betaines and a sample of hair; the amounts of said protease, agent, and detergent being sufficient to effectuate the digestion of the sample;
   (b) permitting the digestion of the sample of hair to form a hair digest solution;
   (c) ensuring that said agent and said protease will not interfere with the accuracy of an immunoassay method performed on the digest solution; and
   (d) subjecting a portion of the hair digest solution to direct analysis by immunoassay.

9. A method for the identification of cocaine, opiates, phencyclidine and methamphetamine from the bloodstream of a subject which becomes embedded in the hair of the subject which comprises:
   (a) preparing a mixture comprising an agent selected from the group consisting of dithiothreitol and dithioerythritol, a protease suitable for the digestion of hair, a detergent selected from the group consisting of cholic acid, deoxycholic acid, colates, deoxycholates, N-tetradecylsulfobetaine, and N-dodecyl-N,N dimethylglycine, and a sample of hair; the amounts of said protease, agent and detergent being sufficient to effectuate the digestion of the sample;
(b) permitting the digestion of the sample of hair to form a hair digest solution;
(c) ensuring that said agent and said protease will not interfere with the accuracy of an immunoassay method performed on the digest solution; and
(d) subjecting a portion of the hair digest solution to direct analysis by immunoassay.

10. A method for the identification of cocaine, methamphetamine, opiates and phencyclidine from the bloodstream of a subject which becomes embedded in the hair of the subject which comprises:
(a) preparing a mixture comprising an agent selected from the group consisting of dithiothreitol and dithioerythritol, a protease suitable for the digestion of hair, and a detergent of the formula:

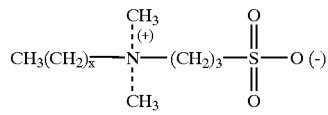

wherein x is in the range of 7–16, and a sample of hair; the amounts of said protease, agent and detergent being sufficient to effectuate the digestion of the sample;
(b) permitting the digestion of the sample of hair to form a hair digest solution;
(c) ensuring that said agent and said protease will not interfere with the accuracy of an immunoassay method performed on the digest solution; and
(d) subjecting a portion of the hair digest solution to direct analysis by immunoassay.

11. A method for the identification of cocaine from the bloodstream of a subject which becomes embedded in the hair of the subject which comprises:

(a) preparing a mixture comprising an agent selected from the group consisting of dithiothreitol and dithioerythritol, a protease suitable for the digestion of hair, a detergent selected from the group consisting of cholic acid, Zwittergents, alkylglucoside, mixtures of alkylglucosides and N-dodecyl-N,N dimethylglycine, and a sample of hair; the amounts of said protease, agent and detergent being sufficient to effectuate the digestion of the sample at a pH below which cocaine will not hydrolyze to benzoylecognine;
(b) permitting the digestion of the sample of hair to form a hair digest solution at the pH; and
(c) subjecting a portion of the hair digest solution to direct analysis by immunoassay to detect the identity of cocaine, if present, in the hair sample.

12. A method for the detection and identification of marijuana from the bloodstream of a subject which becomes embedded in the hair of the subject which comprises:
(a) preparing a mixture comprising an agent selected from the group consisting of dithiothreitol and dithioerythritol, a protease suitable for the digestion of hair, a detergent selected from the group consisting of cholic acid, deoxycholic acid, octyl-B-D-glucopyranoside and octyl-B-D-thioglucopyranoside, and a sample of hair; the amounts of said protease, agent and detergent being sufficient to effectuate the digestion of the sample;
(b) permitting the digestion of the sample of hair to form a hair digest solution; and
(c) subjecting a portion of the hair digest solution to direct analysis by immunoassay to detect the identity of marijuana, if present, in the hair sample.

* * * * *